United States Patent [19]
DeMane et al.

[11] Patent Number: 5,507,830
[45] Date of Patent: Apr. 16, 1996

[54] MODULAR HIP PROSTHESIS

[75] Inventors: Michael DeMane, Memphis; Thomas W. Fallin, Cordova; Steve Garner, Memphis; Jeff Schryver, Cordova; Robert Brosnahan, Germantown, all of Tenn.

[73] Assignee: Smith & Nephew Richards Inc., Memphis, Tenn.

[21] Appl. No.: 128,064

[22] Filed: Sep. 28, 1993

Related U.S. Application Data

[60] Division of Ser. No. 872,818, Apr. 24, 1992, abandoned, which is a continuation-in-part of Ser. No. 470,751, Jan. 31, 1990, Pat. No. 5,108,452, which is a continuation-in-part of Ser. No. 308,205, Feb. 8, 1989, Pat. No. 4,995,883.

[51] Int. Cl.⁶ ........................................... A61F 2/32
[52] U.S. Cl. ................................. 623/23; 623/18
[58] Field of Search ............................... 623/16, 18, 19, 623/20, 22, 23

[56] References Cited

U.S. PATENT DOCUMENTS 3,228,393  1/1966  Michele ................................. 128/92

(List continued on next page.)

FOREIGN PATENT DOCUMENTS

| | | |
|---|---|---|
| 0038897 | 11/1981 | European Pat. Off. ................. 623/23 |
| 0058745 | 9/1982 | European Pat. Off. . |
| 0093230 | 11/1983 | European Pat. Off. . |
| 0202141 | 11/1986 | European Pat. Off. ................. 623/23 |
| 0217034 | 4/1987 | European Pat. Off. ................. 623/23 |
| 0243298 | 10/1987 | European Pat. Off. ................. 623/23 |
| 0257359 | 3/1988 | European Pat. Off. ................. 623/23 |
| 0291562 | 11/1988 | European Pat. Off. ................. 623/22 |
| 0290735 | 11/1988 | European Pat. Off. ................. 623/23 |
| 0295360 | 12/1988 | European Pat. Off. ................. 623/23 |
| 2429010 | 2/1980 | France ................................. 623/23 |
| 2493139 | 5/1982 | France ................................. 623/23 |
| 2610824 | 8/1988 | France . |
| 2633509 | 1/1990 | France . |
| 2318396 | 10/1974 | Germany ............................... 623/23 |
| 2524923 | 11/1976 | Germany ............................... 623/23 |
| 2724041 | 11/1978 | Germany ............................... 623/18 |
| 3336005 | 4/1985 | Germany ............................... 623/18 |
| 600866 | 6/1978 | Switzerland . |
| 0660681 | 6/1987 | Switzerland ........................... 623/22 |
| 2222776 | 3/1990 | United Kingdom . |

OTHER PUBLICATIONS

Hugh U. Cameron, M.B.Ch.B., "Use of a Neck Extension Sleeve in Total Hip Replacement: Technical Note", Contemporary Orthopaedics, Jul. 1990—vol. 21, No. 1.

Leo A. Whiteside, M. D., "Positively Impact Your Clinical Results" Brochure.

*Primary Examiner*—David Isabella
*Attorney, Agent, or Firm*—Pravel, Hewitt, Kimball & Krieger

[57] ABSTRACT

A modular hip prosthesis can be custom fitted to a particular patient by a surgeon prior to surgical insertion. The prosthesis features a body having a neck portion for carrying a rounded head element, a transitional mid-section of the prosthesis body includes generally rectangular and generally rounded cross-sectional areas, and a stem section has a generally rounded cross-sectional area. The stem is tapered to receive a tubular extension sleeve with a hollowed portion corresponding in shape to the stem portion of the prosthesis. The tubular extension sleeve has an open end portion receptive of the lower tapering stem of the prosthesis body. The stem portion includes an internal bore, and an attachment in the form of an elongated screw is provided for connection to the stem internal bore for securing the extension sleeve and the prosthesis body together, forming a compressive sealed connection therebetween. Pads can be attached to the transitional mid-section of the prosthesis body for increasing the cross-sectional shape of the prosthesis at the transitional mid-section. The pads are loaded continuously to connect to the prosthesis body by the hip joint reaction force. Removable collars can be added to the prosthesis to form a transverse load carrying interface with the upper end of the patient's femur. Frustroconically-shaped extension sleeves can be added to the prosthesis neck for extending the neck length.

40 Claims, 8 Drawing Sheets

U.S. PATENT DOCUMENTS

| | | | |
|---|---|---|---|
| 3,585,994 | 6/1971 | Huggler et al. | 128/83 |
| 3,641,590 | 2/1972 | Michele | 3/1 |
| 3,801,989 | 4/1974 | McKee | 3/1 |
| 3,818,514 | 6/1974 | Clark | 3/1 |
| 3,927,660 | 12/1975 | Tegtmeyer | 128/2 A |
| 4,012,796 | 3/1977 | Weisman et al. | 3/1 |
| 4,016,606 | 4/1977 | Murray et al. | 3/1.911 |
| 4,112,522 | 9/1978 | Dadurian et al. | 3/1.91 |
| 4,187,559 | 2/1980 | Grell et al. | 3/1.91 |
| 4,222,380 | 9/1980 | Terayama | 128/216 |
| 4,222,382 | 9/1980 | Antonsson et al. | 128/303 R |
| 4,368,734 | 1/1983 | Banko | 128/305 |
| 4,393,872 | 7/1983 | Reznik et al. | 604/151 |
| 4,399,813 | 8/1983 | Barber | 128/92 |
| 4,404,691 | 9/1983 | Buning et al. | 3/1.911 |
| 4,515,154 | 5/1985 | Leonard | 128/92 |
| 4,578,081 | 3/1986 | Harder et al. | 623/22 |
| 4,608,055 | 8/1986 | Morrey et al. | 623/23 |
| 4,623,353 | 11/1986 | Buechel et al. | 623/23 |
| 4,670,015 | 6/1987 | Freeman | 623/23 |
| 4,676,797 | 6/1987 | Anapliotis et al. | 623/23 |
| 4,693,724 | 9/1987 | Rhenter | 623/23 |
| 4,698,063 | 10/1987 | Link et al. | 623/23 |
| 4,722,331 | 2/1988 | Fox | 128/92 VD |
| 4,738,256 | 4/1988 | Freeman et al. | 128/92 VV |
| 4,770,660 | 9/1988 | Averill | 623/23 |
| 4,770,661 | 9/1988 | Oh | 623/23 |
| 4,777,942 | 10/1988 | Frey et al. | 128/92 VJ |
| 4,790,854 | 12/1988 | Harder et al. | 623/23 |
| 4,840,632 | 6/1989 | Kampner | 623/22 |
| 4,842,606 | 6/1989 | Kranz et al. | 623/23 |
| 4,851,007 | 7/1989 | Gray | 623/23 |
| 4,878,917 | 11/1989 | Kranz et al. | 623/18 |
| 4,883,492 | 11/1989 | Frey et al. | 623/23 |
| 4,908,032 | 3/1990 | Keller | 623/18 |
| 4,921,500 | 5/1990 | Averill et al. | 623/22 |
| 4,938,773 | 7/1990 | Strand | 623/16 |
| 4,995,883 | 2/1991 | Demane et al. | 623/23 |
| 5,015,257 | 5/1991 | Crowninshield et al. | 623/22 |
| 5,032,130 | 7/1991 | Schelhas et al. | 623/23 |
| 5,047,033 | 9/1991 | Fallin | 606/87 |
| 5,066,304 | 11/1991 | Crowninshield et al. | 623/22 |
| 5,108,452 | 4/1992 | Fallin | 623/23 |

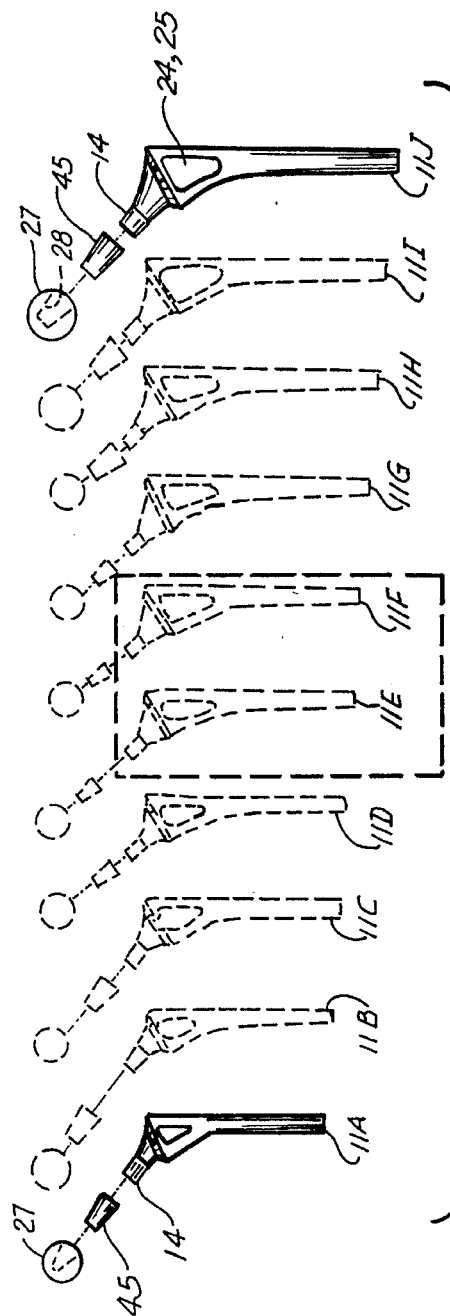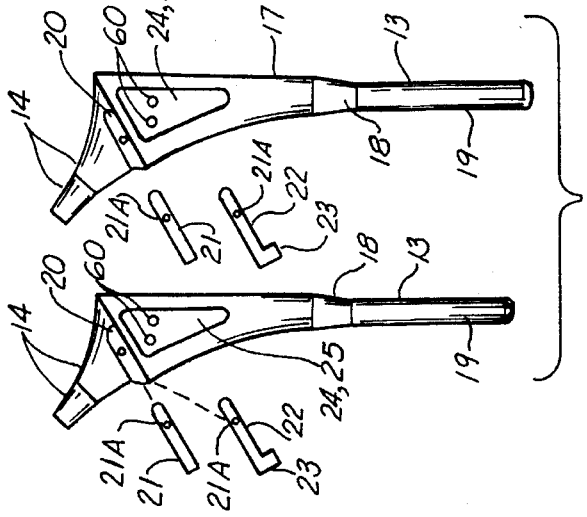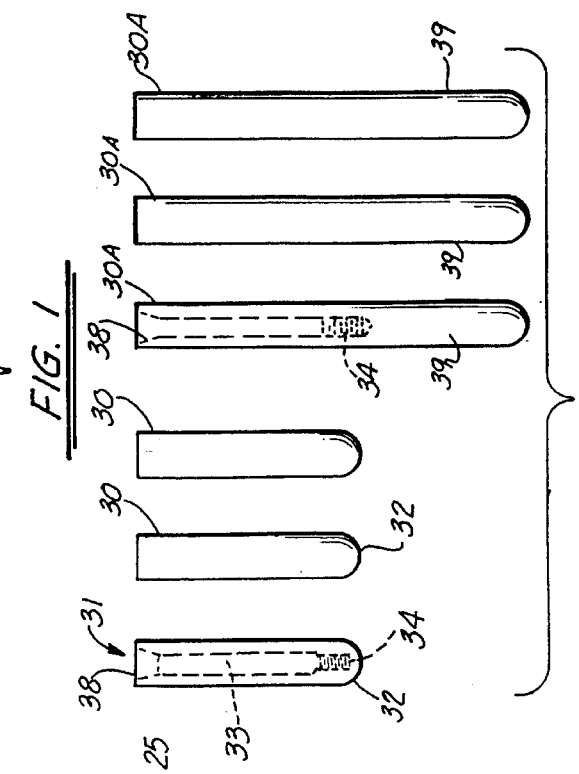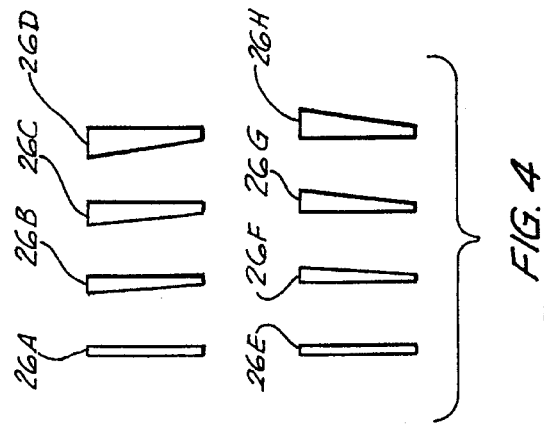

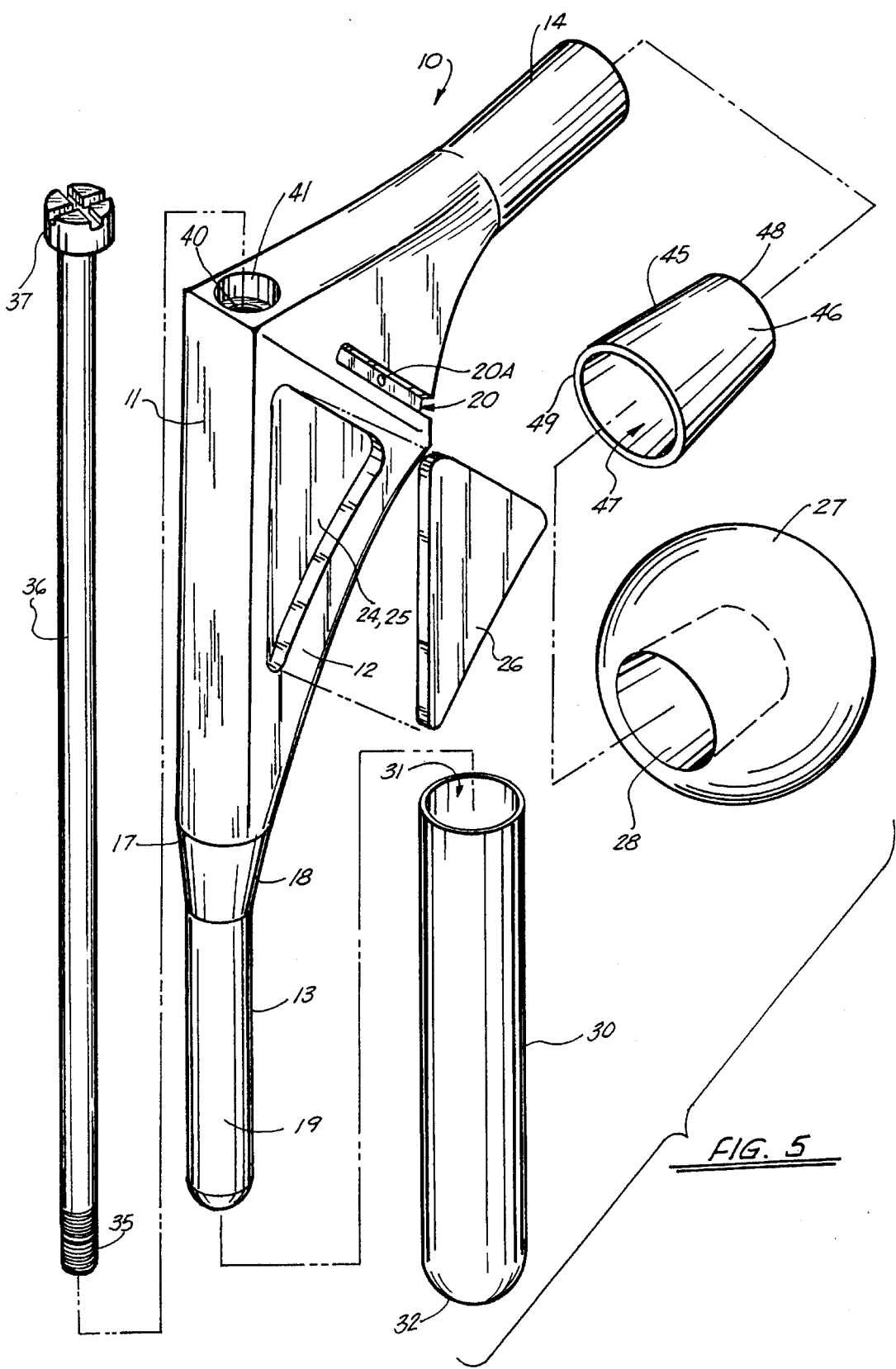

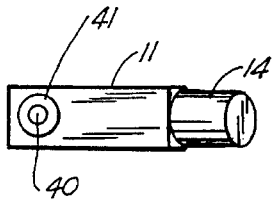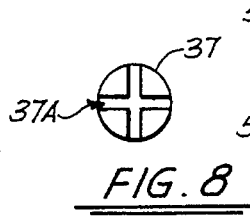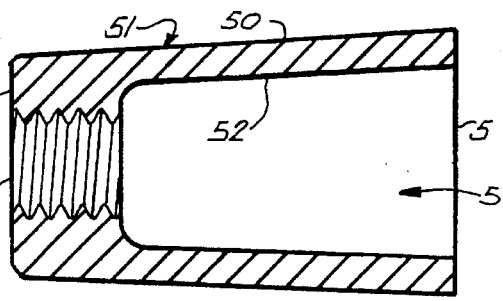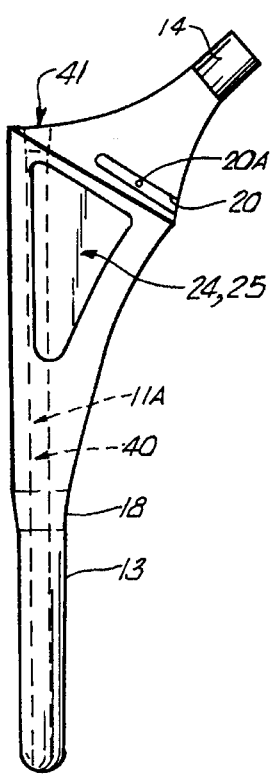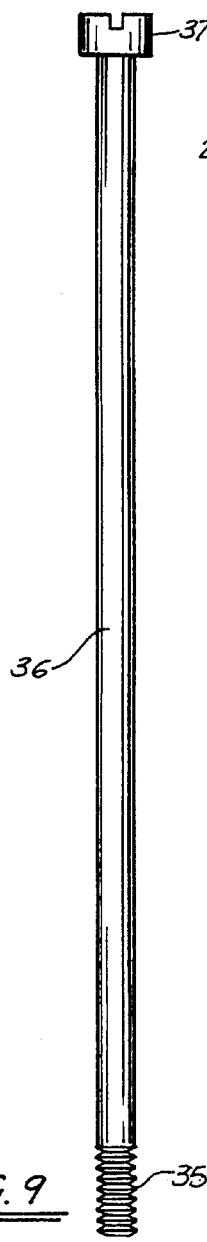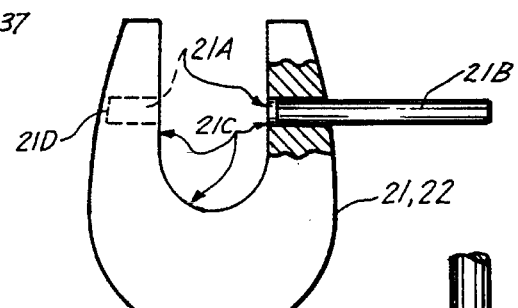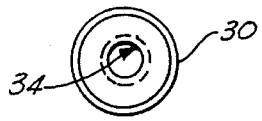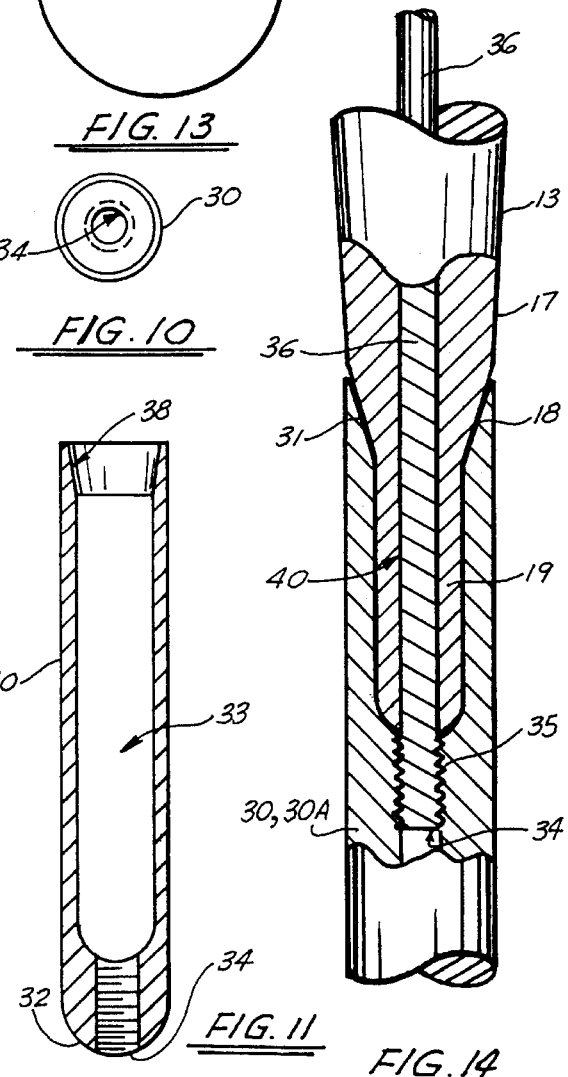

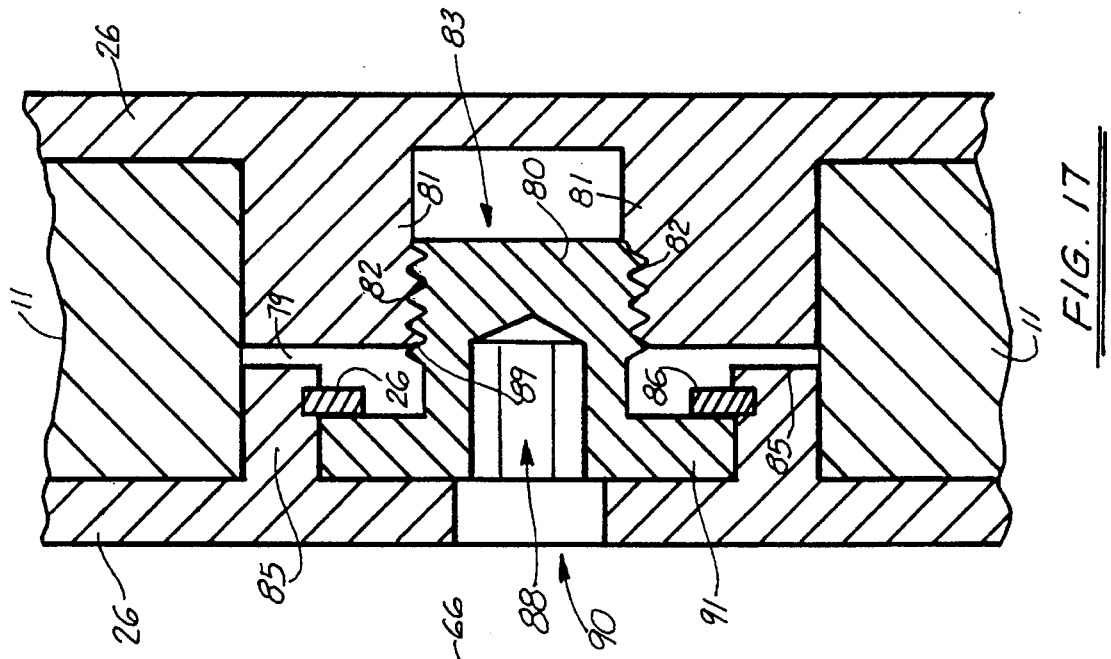
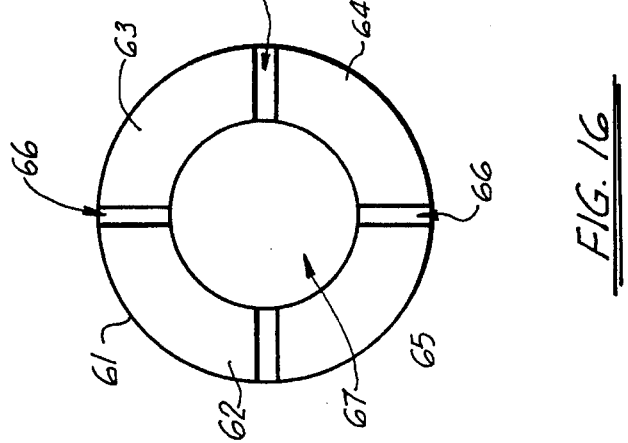
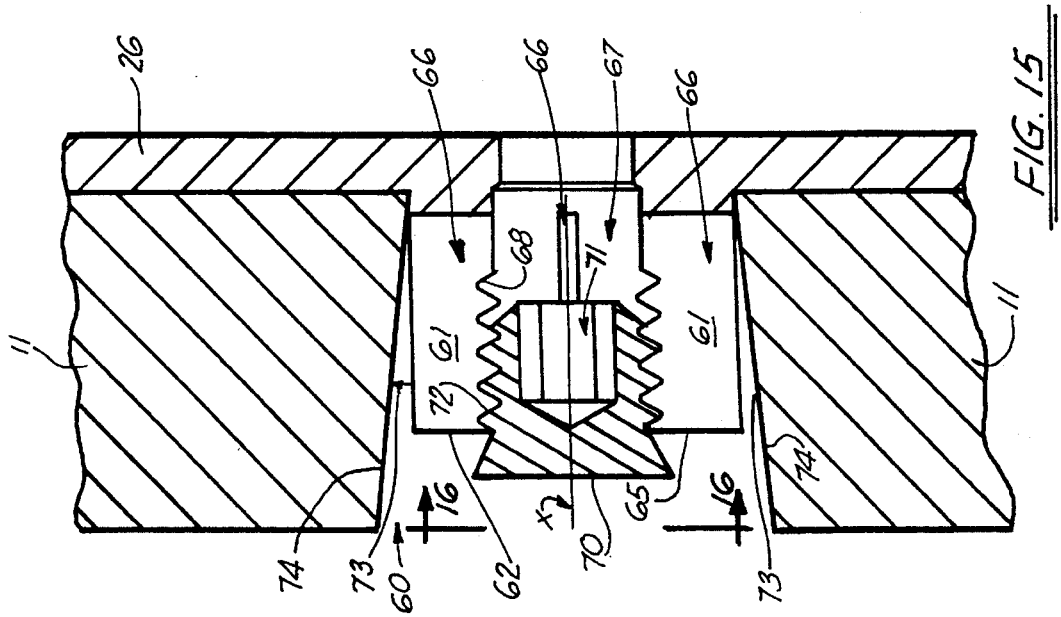

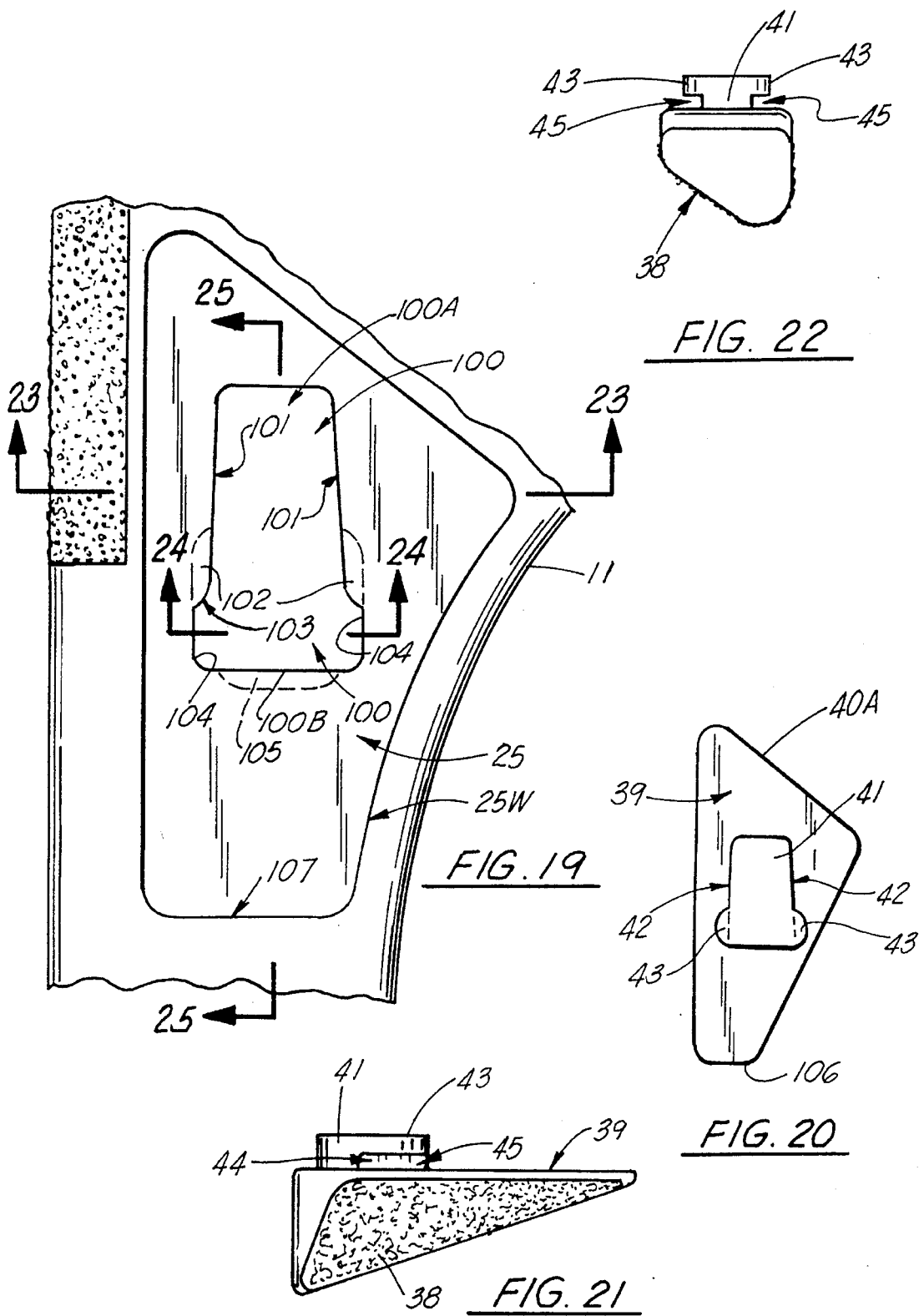

MODULAR HIP PROSTHESIS

CROSS REFERENCE TO RELATED APPLICATIONS

This is a divisional of application Ser. No. 07/872,818 filed on Apr. 24, 1992, now abandoned, which is a continuation-in-part of U.S. patent application Ser. No. 07/470,751, filed Jan. 31, 1990, now U.S. Pat. No. 5,108,452, which is a continuation-in-part of U.S. patent application Ser. No. 07/308,205, filed Feb. 8, 1989, now U.S. Pat. No. 4,995,883, all hereby incorporated herein by reference.

BACKGROUND OF THE INVENTION

1. Field of the Invention

The present invention relates to a modular hip prosthesis system wherein various component parts of an implant kit can be selected during the surgical procedure so that the implant can be custom fitted to a patient, and including removable modular anterior and posterior pads that can be of a variety of custom configurations and sizes are secured with a wedge lock fit connection that continuously self tightens the pads to the prosthesis body during use, as the hip joint reaction force pushes the prosthesis into the femur. Other modular features include removable neck extensions, distal sizers, and modular collars.

2. General Background

Increasingly, surgeons want to be able to custom fit femoral prostheses to patients. Instead of having to choose a properly sized prosthesis from a group of pre-formed implants, it would be advantageous to have a basic design which can be modified with various component parts. This would eliminate the need to maintain a large inventory and would provide better fitting implants.

Custom fitted implants are particularly important in revision cases where an implant has to be removed and replaced since old cement must be removed and bone resorption occurs in many cases. Unpredictable, proximal and/or distal bone loss or deformity often occurs which must be accommodated by the replacement prosthesis.

For initial implants, basic variations in patient anatomy are often confronted by the surgeon. Some patients have femoral necks that can be significantly longer or shorter than others. Cortical shaft defects, which are not uncommon, are not discovered until during operation. Variations in intramedullary canal diameter can also occur, which if not accompanied by a properly sized implant, can result in distal toggle.

In short, it is difficult, if not impossible, to predict the exact shape of a hip implant which is suitable for all patients. Since it is impractical and would be prohibitively expensive to maintain an inventory of implants for most patients, compromises must sometimes be made in supplying implants which fit reasonably well but could be improved upon.

Several hip prostheses are known which are formed of replaceable or interchangeable component parts.

U.S. Pat. No. 3,641,590 entitled "Acetabular Replacement Prosthesis and Method of Assembling" issued to Michele discloses a selective individualized technique for acetabulum socket replacement per se, or in conjunction with a hip replacement prosthesis (referring to the Michele U.S. Pat. No. 3,228,393) for a total hip replacement, designed for all ages including the very young. A selective anchorage for a cup prosthesis of a size selected from the limited number of differently sized cups is made available. Anchorage of the acetabular socket replacement conforms to variations in dimensions, shapes and positions of the (medullary) canals of the acetabulum pelvis of the individual patient and includes at least two elongated and convergent or divergent fasteners.

A removable collar of low modulus of elasticity material is shown in U.S. Pat. No. 4,012,796 entitled "Interpositioning Collar For Prosthetic Bone Insert" issued to Weisman et al. The collar is interpositioned between a collar of a metal prosthetic hip stem implanted in the intramedullary canal of the femur and the adjacent calcar or outer edge of the bone. A flange depends from the insert between the upper portion of the stem and the inner wall of the bone. The interpositioned collar is either a full elongated tapered O-shape or it is open on one side of a tapered U-shape.

U.S. Pat. No. 4,404,691 entitled "Modular Prosthesis Assembly" issued to Buning et al., provides a modular hip prosthesis assembly for replacement of at least part of a joint and part of a bone shaft including a mounting component provided with a connection portion and at least two joint components of similar shape but different dimensions and which can be connected alternatively to the mounting component, each of the joint components having an engagement portion and a connection part adapted for connection to the connection portion of the mounting component, the joint components each providing part of a bone shaft and part of a joint which can cooperate with an appropriate part of a natural or artificial joint.

U.S. Pat. No. 4,578,081 entitled "Bone Prosthesis" issued to Harder et al., discloses a bone prosthesis comprising at least one joint component replacing a natural joint half, which is provided with a shank adapted to be connected to the bone, wherein a set of joint components is provided, and the shank is designed as a bone replacement member, with a connection portion provided adapted to be connected to the bone at one end and at the other end to the shank. One of the components is a hip prosthesis with a rounded head and a hollowed hip component that connects to elongated mounting components. In another hip prosthesis embodiment, a neck with a cone shape receives a suitable joint head with an inner cone.

A femoral component for hip prosthesis is shown in U.S. Pat. No. 4,608,055 issued to Morrey et al., the prosthesis disclosed in the '055 patent includes a stem portion and a combined integral head and neck portion. The stem portion includes a proximal portion and a distal portion which are angularly related with respect to one another and with the proximal portion including a recess formed therein for receipt of the tapered portion of the head and neck component. The head and neck component includes a substantially part spherical head portion attached to a neck portion and a tapered portion angularly attached to the neck portion via a basilar neck portion with the tapered portion being adapted to be permanently inserted into the recess portion of the proximal end of the above described stem portion. The stem portion includes a plurality of recesses on the periphery and longitudinal extent thereof for receiving fiber metal pads which are provided to allow boney ingrowth therein in order to retain the femoral component permanently installed in the proximal end of the femur.

In U.S. Pat. No. 4,676,797 entitled "Unit For Resection Prosthesis", a resection prosthesis assembly unit includes a head member, an end member and an intermediate member between the head and end members, of which one member is provided with a conical pin and another member is provided with a conical pin and another member is provided with a conical bore. The latter two members are provided with respective first surfaces that extend transversely to an insertion direction and which face one another and are spaced apart to define a recess when the two members are connected together. One of the two members is further provided with a second surface extending in the insertion direction, and the recess being provided to receive a wedge insertable into the recess to bear against the first surfaces for forcing the two members apart while the forces exerted by the wedge are absorbed by the first surfaces and the wedge is guided by the second surface.

Additionally, end fitting distal sizers attached in a similar fashion could allow the surgeon to tailor the prosthesis tip to the canal diameter thereby reducing distal toggle.

SUMMARY OF THE INVENTION

The present invention provides a modular hip prosthesis which can be custom fitted to a particular patient by a surgeon prior to surgical insertion of the prosthesis.

The apparatus includes a prosthesis body having a generally wider larger, i.e., upper mid-section portion and an upper neck adapted for carrying a rounded head portion that fits either the patient's acetabulum or a prosthetic acetabular component.

A lower stem extends from the mid-section and terminates at a lower rounded tip. The stem is adapted for placement in the intramedullary canal of the patient's femur. Distal stem sizers are provided which allows the length of the femoral shaft to be augmented with extensions that lock with the primary shaft using a tapered attachment. This attachment allows the surgeon to extend the stem length beyond any cortical shaft defect he may encounter intraoperatively.

The distal sizer in preferably the form of a tubular stem extension sleeve includes a hollowed portion corresponding in shape to the stem. The sizer includes an open end portion which is receptive of the stem for insertion thereinto. The lower stem portion includes an internal bore. Corresponding frustroconical surfaces of the distal sizer and stem allow a tight fit to be achieved between distal sizer and stem. In another embodiment, an attachment member, preferably in the form of a threaded draw bolt, forms an attachment between the internal bore of the stem and the extension sleeve holding the extension sleeve to the prosthesis body.

The stem and sleeve corresponding tapered or frustroconical surfaces form a tight friction fit which seals wear particles from body tissues that typically wear off during insertion of the stem to the sleeve. A commercially available impact driver tool can load the sleeve to the stem, and the corresponding tapered regions register very tightly together forming a seal and an interference like fit.

In one embodiment, when a draw bolt is tightened, its non-threaded end presses against the hip stem to provide tension in the bolt and compressive force between the stem and sleeve in corresponding tapered regions of the stem and sleeve.

The tubular stem extension sleeve is of a generally uniform cross-section. Its upper end has an annular tapered section that registers with correspondingly tapered section of the stem. The prosthesis body in one embodiment has a longitudinal central open ended bore that extends substantially the length of the prosthesis body. The attachment includes an elongated fastener, preferably an elongated threaded bolt that is adapted for placement within the elongated bore, extending substantially the length of the bore upon assembly. The bolt provides an upper head end portion which can be manipulated by the surgeon at the top of the prosthesis for tightening or loosening the fit between the sleeve and prosthesis body.

The stem extension sleeve provides a threaded section that can engage the lower end portion of the bolt to form a threaded connection. This attachment of sleeve and prosthesis body can also be made using a very short bolt which is affixed through an opening in the bottom of the extension sleeve, and into a bore in the bottom of the stem. The stem extension sleeves can be of varying lengths and diameters, and can be straight or curved. The sleeve hollow bore portion can extend substantially the length of the sleeve, or can extend a partial distance along the sleeve.

The assembly draw bolt can be tightened after the prosthesis and extension sleeve are in position so that the extension can twist to track the intermedullary canal during insertion. After placement, the draw bolt can be used to lock the extension and prosthesis body together.

The prosthesis body has a frustroconically-shaped neck portion for carrying a rounded head element. Between the neck portion and the distal end is a transitional mid-section having generally rectangular upper cross-sectional area and a generally rounded lower cross-sectional area. Extension sleeves having conical inner and outer surfaces and can be added to the neck portion for elongating the neck portion with respect to the prosthesis body and the head.

Removable transverse bearing collars can be adjustably affixed to the mid-section of the prosthesis body, generally transverse to the longitudinal axis of the prosthesis body for forming a load carrying interface between the prosthesis body and the upper end of the patient's femur. In one embodiment, the removable bearing collar can have extensions that will compensate for proximal bone loss, i.e. at the top of the patient's femur.

Removable pads are attachable to the mid-section of the prosthesis for changing the cross-sectional configuration of the prosthesis at the mid-section. One or more sockets are formed in the prosthesis at the mid-section for carrying the modular pads. In one embodiment, a wedge lock connection secures each pad to the prosthesis body. A locking member on the back of each pad locks each pad to the prosthesis at corresponding engaging wedge surfaces thereon. The pads each carry corresponding locking tab members which insure complete interlocking engagement of the pads to the prosthesis body before forming the wedge lock connection. This safety feature requires that the surgeon fully engage each pad into its socket before being able to slide the pad into the wedge-lock position. The tabs on the locking member of each pad engage a recess or undercut in the socket of the prosthesis body to constrain the pad from moving in a direction away from the prosthesis body, after assembly is completed.

Pad shape can be varied to custom fit the patient's anatomy maximizing stability to transfer shear load or compression load between the prosthesis and the patient's bone as desired. The pads can be of differing materials such as porous or roughened coatings to promote tissue ingrowth or on growth. Also, manufacturing methods which might weaken the integrity of the prosthesis body, such as the addition of a coating of beads, can be used for the removable pads, thus not affecting the structural integrity of the prosthesis body.

BRIEF DESCRIPTION OF THE DRAWINGS

For a further understanding of the nature and objects of the present invention, reference should be had to the following detailed description, taken in conjunction with the accompanying drawings, in which like parts are given like reference numerals, and wherein:

FIG. 1 is a side view illustrating a plurality of hip prosthesis bodies as used with the modular hip system of the present invention;

FIG. 2 is a side view of a pair of hip prosthesis bodies of differing sizes illustrating insertion of the modular collar portions thereof;

FIG. 3 is a side view illustrating a plurality of sleeve extension parts as used in the modular hip prosthesis system of the present invention;

FIG. 4 is a side view of a plurality of modular pads for use with the hip prosthesis bodies of FIGS. 1 and 2, illustrating varying pad cross-sectional configurations;

FIG. 5 is a perspective exploded view illustrating the preferred embodiment of the apparatus of the present invention;

FIG. 6 is a top view of the prosthesis body portion of the preferred embodiment of the apparatus of the present invention;

FIG. 7 is a side view of the prosthesis body portion of the preferred embodiment of the apparatus of the present invention;

FIGS. 8 and 9 are top and side views illustrating the assembly bolt portion of the preferred embodiment of the apparatus of the present invention;

FIGS. 10 and 11 are top and side sectional views of the stem extension sleeve portions of the preferred embodiment of the apparatus of the present invention;

FIG. 12 is a sectional view illustrating an alternate construction of the neck extension sleeve portion of the preferred embodiment of the apparatus of the present invention;

FIG. 13 is a plan view illustrating the modular collar portion of the preferred embodiment of the apparatus of the present invention;

FIG. 14 is a partial sectional view illustrating the preferred embodiment of the apparatus of the present invention with the prosthesis body and stem extension sleeve assembled;

FIG. 15 is a sectional elevational fragmentary view illustrating the assembly of modular pads to the prosthesis body;

FIG. 16 is a sectional view taken along 16—16 of FIG. 15;

FIG. 17 is a sectional elevational view of a second construction of the preferred embodiment of the apparatus of the present invention illustrating the assembly of the modular pads to the prosthesis body;

FIG. 19 is a side fragmentary view of the second embodiment of the modular hip prosthesis of the present invention;

FIG. 20 is a rear view illustrating the construction of the modular pad of the second embodiment of the apparatus of the present invention;

FIG. 21 is a side view illustrating the construction of the modular pad of the second embodiment of the apparatus of the present invention;

FIG. 22 is an end view illustrating the construction of the modular pad of the second embodiment of the apparatus of the present invention.

DETAILED DESCRIPTION OF THE PREFERRED EMBODIMENT

Figure 18:
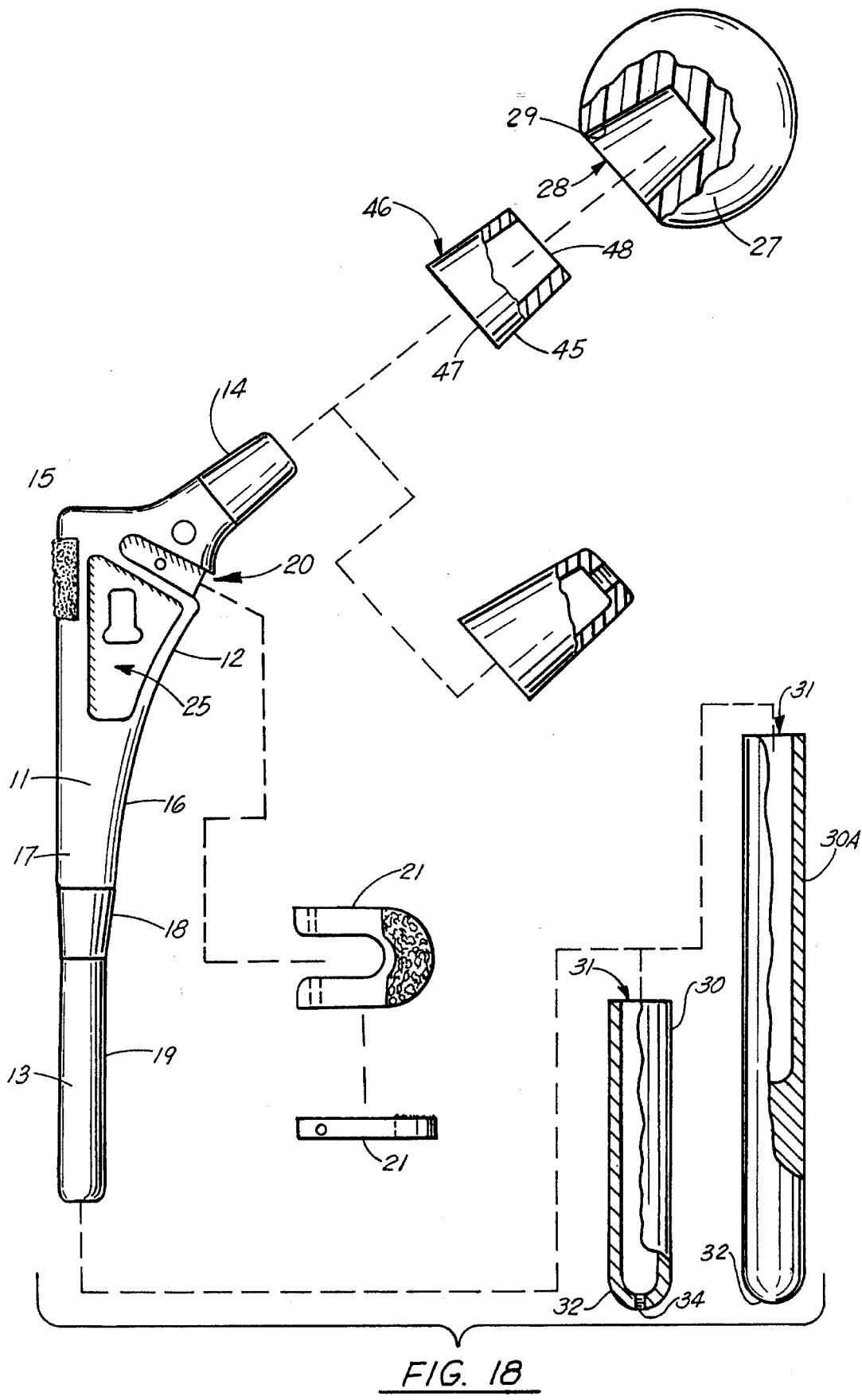
FIG. 18 is a side exploded view of a second embodiment of the modular hip prosthesis pads of the present invention.
Figure 23:
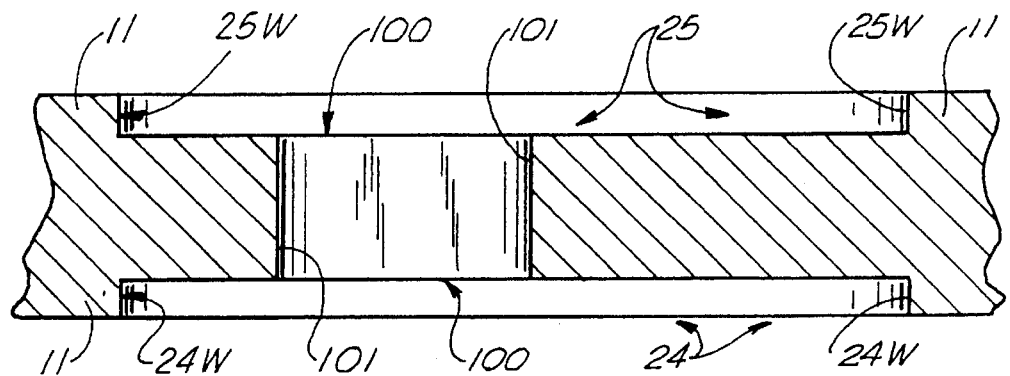
FIG. 23 is a sectional view taken along lines 23—23 of FIG. 19.

FIGS. 1–5 illustrate generally the preferred embodiment of the apparatus of the present invention designated generally by the numeral 10. In FIG. 5 there can be seen a prosthesis body 11 which includes a widened mid-section 12, a lower elongated generally cylindrically shaped stem 13 and an upper neck 14. The mid-section includes an upper generally rectangular cross-sectional portion 15 and a lower generally rounded cross-sectional portion 16 which communicates with the generally cylindrical stem 13.

The stem 13 includes three sections including an upper larger cylindrical section 17, a frustro-conical tapered transition section 18 and a lowermost smaller-diameter cylindrical portion 19. The prosthesis body 11 would preferably be supplied to hospitals and surgeons in kit form with a plurality of prosthesis bodies 11, modular pads 26, heads 27, collars 21, 22 and extension sleeves or distal sizers 30 being offered in various sizes such as is shown in FIGS. 1–2, including prosthesis bodies 11A–11J, pads 26A–26H and sleeves 30, 30A.

Each prosthesis body 11 includes a generally U-shaped annular recess 20 which extends around one edge of the transitional mid-section 12 portion of the body 11 and is receptive of generally U-shaped collars 21 or 22 (FIG. 2). Recess 20 has a shape corresponding to the inner edge portion 21C of collar 21. Collar 21 is thus generally U-shaped in plan view (FIG. 13). Another embodiment of U-shaped collar 22 provides a similar, generally U-shaped body in plan view, but also includes a downwardly extending tab 23 which can be used to help transfer load between the prosthesis 10 and the femur where proximal bone tissue has eroded.

Lock pin 21B (FIG. 13) extends through openings 20A, 21A in order to secure collars 21, 22 to prosthesis body 11. One of the openings 21A can be formed as a blind socket hole with a transverse closure wall 21D and thus not extend all the way to the outer surface of the collar so that the pin 21B cannot be driven too far and project from the outer surface of the collar 31.

Each prosthesis body 11 includes a pair of left and right sockets 24, 25 which are receptive of one or more adjustment pads 26A—26H. The cross-sectional configuration of each pad 26A—26H can vary including thicker portions of the pad at the top as compared with the thickness at the bottom such as for example can be seen in FIG. 4 with pad 26D and pad 26H which are thicker at one edge as compared with pads 26A and 26E. The pads 26A—26H can be added by the surgeon to give a custom fit to the prosthesis body 11 in the area of the mid-section 12.

Neck 14 is a frustroconically-shaped neck receptive of head 27 and of frustroconical neck extension sleeves 45. Head 27 provides a socket 28 corresponding in shape to neck 14. A plurality of heads 27 can be provided in various sizes as part of the kit, for matching each respective prosthesis body 11A–11J.

Each stem 13 is preferably rounded at its lower tip. The lowermost portion 19 of stem 13, which is of a smaller diameter, and the frustro-conical transition portion 18 of stem 13 form an attachment with a stem extension sleeve 30 (FIGS. 3, 5, 10, 11, and 14). The sleeve 30 is elongated and generally cylindrical and has an open end 31 which allows insertion of the stem 13 thereinto. The lowermost end portion of the sleeve 30 includes a generally curved distal end portion 32.

Extension sleeve 30 is hollow providing a longitudinally extending bore 33 which extends between open end 31 and threaded aperture 34. Aperture 34 extends downwardly from bore 33, communicating with end 32. Threaded aperture 34 is receptive of the external threads 35 of a draw bolt 36. Bolt 36 includes an uppermost head portion 37 and a lower threaded portion 35. Prosthesis body 11 thus includes a longitudinally extending central bore 11A that is receptive of elongated bolt 36.

The upper end portion of extension sleeves 30, 30A includes a frustro-conical inner annular surface (FIGS. 3 and 11) which corresponds in shape to the frustro-conical transition portion 18 of stem 13 so that extension sleeves 30, 30A and stem 13 can form a frictional tight fit upon assembly (see FIG. 14). Draw bolt 36 would be tightened after placement of prosthesis body 11 and a sleeve 30 or 30A into the intramedullary canal. Thus the extension sleeve 30 or 30A can have a flexibility by using a thin wall thickness, for example, so that it is free to track the natural path of the intramedullary canal during insertion. After insertion, bolt 36 is tightened, drawing the frustro-conical inner surface of sleeve 30, 30A and transition portion 18 of stem 13 together.

Extension sleeve 30 can be a short version having a longitudinally extending bore 33 which communicates with aperture 34, extending to end 32. In another embodiment (see FIG. 3), extension sleeve 30A can be elongated extending well beyond threaded aperture 34. As shown in the longer sleeve in FIG. 3, the longitudinal axis of extension sleeve 30A can change angle slightly or have a curvature in order to track the intramedullary canal, with the lower end portion 39 of each extension sleeve 30A being solid and being slightly skewed with respect to the longitudinal axis of open bore 33. This allows the extension sleeve 30A to track the natural path of the intramedullary canal which is not perfectly straight nor a pure elongated cylinder. Thus, the elongated extension sleeves 30A can curve or bow to conform naturally to the femur of a patient for a custom fit.

A plurality of heads 27 of differing sizes would be provided. The distance between the prosthesis body and the head 27 could be varied using extension members 45 or 50. Extension member 45 would be a hollowed trunion structure, having a conical outer surface 46 and a corresponding conical inner surface 47. A smaller open end portion 48 and a larger open end portion 49 define therebetween a bore which is occupied by neck 14 upon assembly of extension member 45 thereupon. Because of the smaller end 48, a head 27 could simply be slipped upon the extension member 45 with the socket 28 of head 27 registering upon the outer surface 46 of the extension member 45. An impact driver could load a selected extension member on the head 27 with a predetermined load, with the conical surfaces fitting tightly together. In the preferred embodiment, extension members 45 of differing lengths and of different cross-sectional dimensions would be provided to correspond to the plurality of differing neck sizes that accompany the plurality of prosthesis bodies as provided in kit form (see FIG. 1). An alternative construction of neck extension members is shown in FIG. 12 wherein the extension member 50 includes a conical outer surface 51, a conical inner surface 52 with a small end portion 53 having a threaded opening 54 that communicates with socket 56 at large diameter end portion 55 of extension member 50. Thus, the socket 28 of a particular selected head 27 would be registered tightly upon the end of extension member 50 in a wedge fit fashion. In order to remove the member 50 from neck 14, the threaded opening 54 would be threadably engaged with a removal tool in the form of an elongated shaft having one end portion which is threaded and the opposite end portion defining a handle, and/or an inertia weight sliding along the shaft, for example.

In FIGS. 15–17, pads 26 are shown as removably attached to prosthesis body 11. In FIG. 15, it should be understood that only the assembly for securing one pad 24 or 25 is shown.

In the embodiment of FIG. 17, the pads 26 are held in place by a single attachment mechanism that is carried generally between the pads 26 forming a connection therebetween.

In the embodiment of FIG. 15 there is provided an annular bushing 61 which is an extension of each pad 26. Bushing 61 includes a plurality of arcuate members 62–65 with spaces 66 therebetween so that the bushing 61 can expand and grip the beveled annular wall 74 of opening 60 in prosthesis body 11 which is doubled. A bolt 70 is threadably attached to threaded bushing 61 so that the threads 72 of bolt 70 register with and threadably engage the threads 68 of bushing 61. Upon such threadable connection, the individual arcuate members 62–65 of bushing 61 expand (see arrows 73 of FIG. 15) bearing against the annular wall 74 of opening 60. An opening 67 in pad 26 communicates with a tooled opening 71 in bolt 70 so that a tool such as an allen wrench for example can be inserted through opening 67 and into registration with the slot 71 which would be correspondingly shaped to receive the tool used.

In the embodiment of FIG. 17, a single assembly bolt 80 is used to secure a pair of pads 26 together upon prosthesis body 11. The prosthesis body 11 includes a cylindrical transverse opening 79 which is occupied by annular bushing 81 integrally attached to pad 26. Bushing 81 includes an inner socket portion 83 which is threaded with internal threads 82. Assembly bolt 80 provides corresponding external threads 89 which threadably engage the threads 82 of bushing 81. A socket 88 is receptive of a tool such as an allen wrench for example and rotates therewith to tighten pads 26 together. Pad 26 provides a bushing 85 which carries an annular retaining ring 86, which can be a split ring or the like. An opening 90 allows access through pad 26 to the tooled opening 88. Assembly bolt 80 includes a generally circular annular head portion 91 which is held against pad 25 with ring 86. As the threaded bolt 80 is tightened, pads 26 are thus pulled together and tightly against prosthesis body 11.

FIGS. 18–25 illustrate an alternate embodiment of the apparatus of the present invention wherein removable pads 40A, 40B attach to prosthesis body 11 with a wedge fit that self tightens the connection between each pad 40A, 40B and the prosthesis as hip joint reaction force pushes the prosthesis into the femur during use. A safety feature of each pad 40A, 40B and prosthesis body 11 connection is a locking member with tabs that force the surgeon to fully engage the pad 40A, 40B into a provided opening 100 on the prosthesis body 11 before a sliding of the pad 40A, 40B into locking engagement with the prosthesis body 11.

In FIG. 19, there can be seen a fragmentary view of prosthesis body 11 having a socket 25 therein with a peripheral edge wall 25W. Similarly, the opposite side of prosthesis body 11 would have a socket 24 providing a peripheral side wall 25W. Each socket 24, 25 receives a modular pad 40A, 40B respectively. In FIGS. 19–22, pad 40A is shown which registers during operation with the pad socket 24. The modular pad 40B would be a mirror image of the views shown for pad 40A of FIGS. 20–22.

Figure 24:
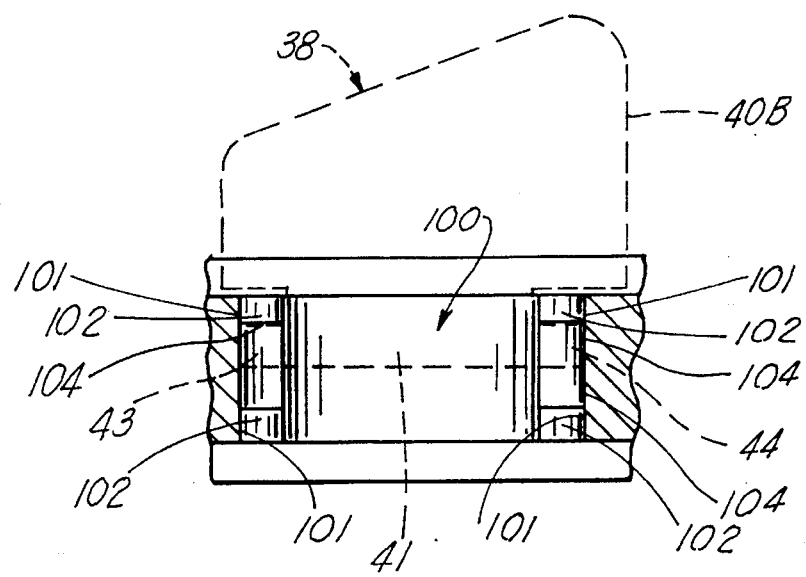
FIG. 24 is a sectional view taken along lines 24—24 of FIG. 19.
Figure 25:
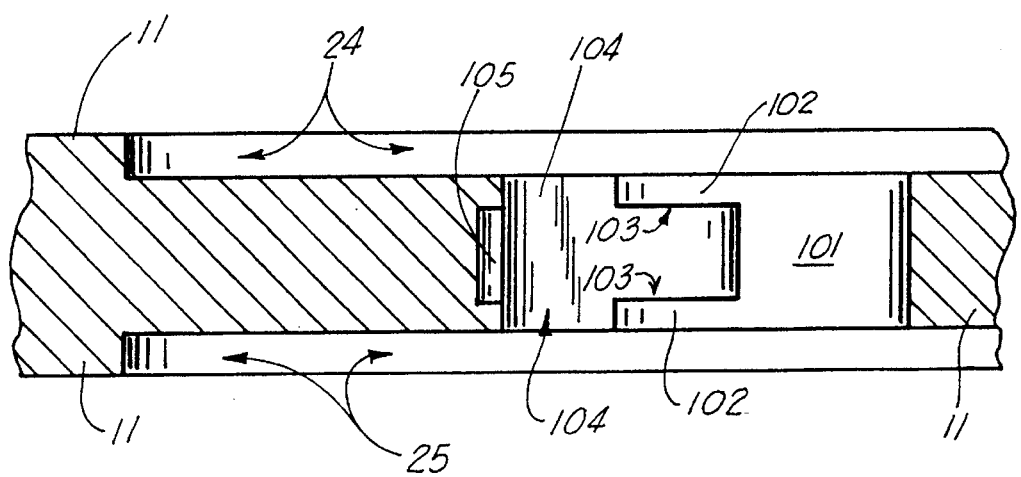
FIG. 25 is a sectional view taken along lines 25—25 of FIG. 19.

Each modular pad 40A, 40B carries on its rear surface 39 a wedge locking member 41 having a pair of opposed inclined locking surfaces 42 which form an acute angle with respect to one another, as shown in FIG. 20. During use, the surgeon places modular pad 40A into its similarly shaped socket 24 registering the locking member 41 into opening 100. The locking member 41 carries a pair of tabs 43 which initially register at the enlarged end portion 100B of opening 100. Similarly, the inclined locking surfaces 42 of locking member 41 register with similarly shaped locking surfaces 101 of opening 100. The tabs 43 must be registered with the enlarged 100B end of opening 100. Otherwise, the locking member 41 will not fit into the opening 100. This provides a safety feature because the surgeon must fully place the particular pad 40A, 40B into its socket 24, 25 before attempting to wedge lock the pad 40A, 40B to the prosthesis body 11. Once the locking member 41 has been fully registered within the opening 100, the surgeon then simply slides the pad upwardly toward the upper end 15 of the prosthesis body 11. The tabs 43 then slide under shoulders 102 and register in undercut slots 103, as shown in FIG. 24. As each pad 40A, 40B is moved into locking position by the surgeon, the surfaces 42 of the wedge locking member 41 engage the inclined surfaces 101 of the opening 100. A tight wedge-lock fit is obtained by forcing the surfaces 42, 101 together using an impact driver or a mallet and a hand held driver element or punch. Each pad 40A, 40B secures tightly to the prosthesis body because the surfaces 42 wedge fit to the surfaces 101.

In the preferred embodiment, the outer periphery of each pad 40A, 40B has a shape corresponding to the peripheral wall 24W, 25W of each socket 24, 25. However, the pads 40A, 40B are sized slightly smaller than the outer configuration of each socket 24, 25 as defined by their peripheral side walls, 24W, 25W. This provides room to move each pad 40A, 40B slightly so that sliding action can be used to perfect the wedge lock connection between each pad 40A, 40B and its respective socket 24, 25. Thus, the outer edge of each pad 40A, 40B would be spaced inwardly from the peripheral wall 24W, 25W of each socket 24, 25 by a small measure.

A very tight wedge lock connection can be formed between each pad 40A, 40B and the prosthesis body 11 using an impact driver. In the preferred embodiment, each pad includes a generally flat lower surface 106. A similar flat surface 107 is provided at the bottom of each socket 24, 25. However, upon manual assembly of the pads 40A, 40B to the prosthesis body 11 by the surgeon, an impact driver can be used to tighten the pads 40A, 40B to the prosthesis body 11 using the impact driver. An impact driver is a commercially available product which carries a tooled end portion having, for example, a commercial screw driver tip or wedge tip. The impact driver tool tip (not shown) is then placed in the space formed between the surfaces 106 and 107 after the surgeon places the respective pads 40A, 40B in their respective sockets 24, 25. The prosthesis is placed on a flat surface and the surgeon simply presses downwardly on the impact driver, activating the tool tip portion of the impact driver to force the surface 106 away from the surface 107. The surgeon then turns the prosthesis over and repeats the same procedure for the second pad. It has been found that using a commercially available, relatively small impact driver, such as supplied by Starrett Company, as much as 300 pounds of load can be generated holding each pad 40A, 40B to the prosthesis body 11.

In the event that one of the pads 40A or 40B were to become loose, because the surgeon possibly did not apply enough force to the pad in order to wedge lock it to the prosthesis body 11, the present invention provides a safety feature for continuously loading each pad 40A, 40B to the prosthesis body 11. This is insured because the pad outer surface 38 is typically beveled so that the bottom of the pad is narrower and the top of the pad is wider, as shown in FIGS. 21 and 22. Thus, when the pad is installed, it self tightens as the hip joint reaction force of the patient pushes the prosthesis further into the femur. The femur presses on the outer surface 38 of the pad, forcing it upwardly and further forcing the wedge lock surfaces 42 of each pad 40A, 40B against the surfaces 101 of the opening 100.

An additional safety feature of the present invention is that the walls 24W, 25W of the sockets 24, 25 contain the pads 40A, 40B if the pads are inadvertently disengaged from the locking mechanism.

Another safety feature of the present invention are the locking tabs 43 which force the surgeon to fully engage the pads 40A, 40B into their respective slots 24, 25 before attempting to slide the wedge inclined locking surfaces 42 into engagement with the locking surfaces 101. If the surgeon does not fully engage the pads 40A, 40B into opening 101, the locking tabs prevent wedge locking of the surface 42 to the surface 101.

The present invention provides thus a simple and quick modular pad construction that allows for installing different contours on either the anterior or posterior side of the prosthesis so that the femoral cavity can be completely filled in order to obtain a better bone-prosthesis contact. The present invention could be supplied with a number of trial sockets in kit forms so that the kit could be used to size the apparatus perfectly. Then, the surgeon would have the actual prosthesis and its modular pads in pre-packaged sterilized condition. Thus, the surgeon could use the trial kit to size the prosthesis and its modular parts and then simply open the corresponding part from a sterile package when the correct fit had been obtained.

Figure 26:
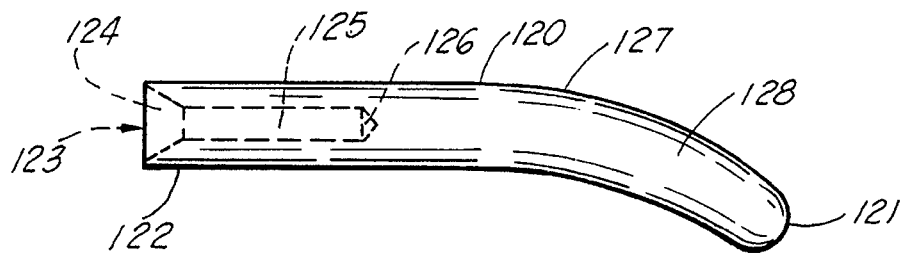
FIG. 26 is a side sectional view of a distal sizer for use with the modular hip prosthesis system of the present invention.

FIGS. 26–29 illustrate an alternate embodiment of the distal sizer designated by the numeral 120 in FIG. 26. Distal sizer 120 includes a lower hemispherically-shaped distal end portion 121 and upper end portion 122 which attaches to the stem 13 of prosthesis body 11 of FIGS. 1, 2 and 5. In FIG. 26, a bore 123 communicates with the uppermost or proximal end 122 of distal sizer 120.

Bore 123 includes a frustroconical section 124 and a generally cylindrical section 125 terminating at conically-shaped end portion 126. The distal sizer 120 provides a curved section 128 that begins at the middle 127 portion of the distal sizer 120 and terminates at distal end 121 thereof.

Figure 27:
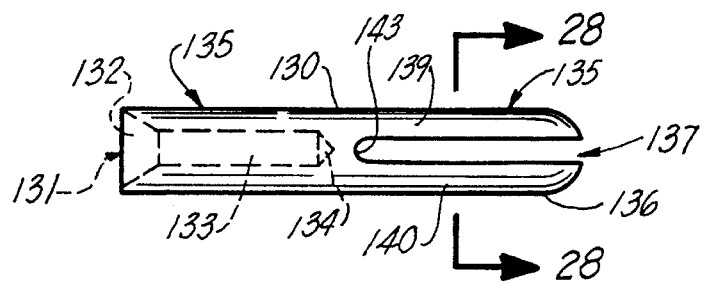
FIG. 27 is a side view of an alternate embodiment of the distal sizer portion of the modular hip prosthetic system of the present invention.
Figure 28:
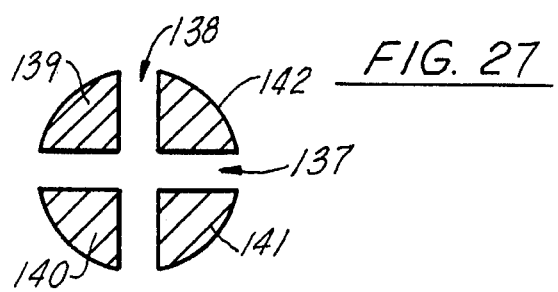
FIG. 28 is a sectional view taken along lines 28—28 of FIG. 27.

In the embodiment of FIG. 27, a distal sizer 130 is provided having a bore 131 which includes a frustro-conical portion 132, a generally cylindrical section 133, and a conical end portion 134. The prosthesis 130 outer wall 135 is generally cylindrically shaped. The lower or distal end portion 136 provides a pair of longitudinally extending and intersecting slots 137, 138. The slots 137, 138 form a plurality of distal sizer segments 139–142, as shown in FIG. 28. Each of the slots 138, 137 terminates at 143 which is at the central portion of distal sizer 130.

Figure 29:
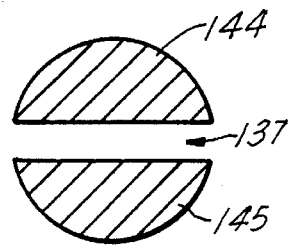
FIG. 29 is an end view of the distal sizer of FIG. 27.

In the embodiment of FIG. 29, a single slot 137 is illustrated which forms a pair of distal sizer segments 144, 145. In the embodiment of FIG. 29, the distal sizer would be constructed like the embodiment of FIG. 27 with the exception that a single slot 137 is provided rather than the two slots 137, 138 of the embodiment of FIGS. 27–28.

Figure 30:
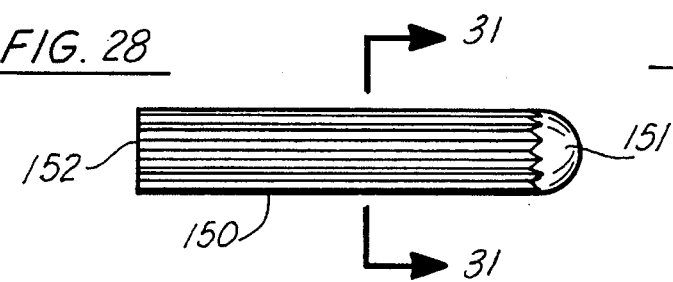
FIG. 30 is a side view of another alternate embodiment of the distal sizer portion of the modular hip prosthesis system of the present invention.
Figure 31:
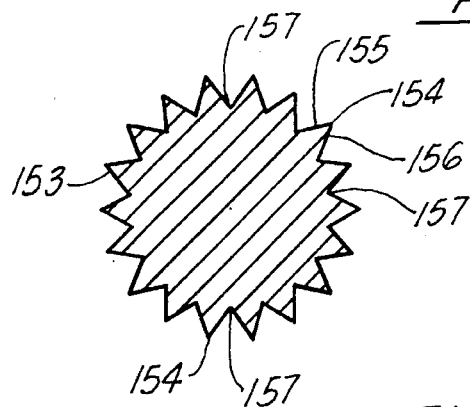
FIG. 31 is a sectional view taken along lines 31—31 of FIG. 30.

In FIGS. 30–31, a further embodiment of the distal sizer is provided designated as 150. Distal sizer 150 provides a hemispherically-shaped lower end portion 151 and an upper end portion 152. The distal sizer 150 is provided with an internal bore of the shape and configuration of the bores 131 of FIGS. 26 and 27. This would provide for attachment of the sizer 152 to the stem 13 of prosthesis body 11 of FIG. 5, for example.

The distal sizer 150 is generally cylindrically shaped in cross-section but provides a plurality of circumferentially spaced, longitudinally extending projections 153. Each projection 153 has a trough 154 and a pair of sidewall 155, 156 portions with a crest 157 between adjacent projections 153.

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A modular hip prosthesis that can be custom fitted to a particular patient by a surgeon prior to surgical insertion, comprising:
    a) a hip prosthesis body having an upper, proximal end portion that provides a neck adapted for carrying a rounded head portion that fits the patient's acetabulum, a thickened mid-section with anterior and posterior sides and a lower generally cylindrically-shaped distal stem portion having upper and lower ends, said prosthesis body being adapted for placement in the intramedullary canal of the patient's femur;
    b) a plurality of removable distal extension sleeve members at least a portion of each of said sleeve member having a hollow bore configured for receipt and attachment, respectively to the cylindrically-shaped distal stem portion for selectively conforming the prosthesis to the adjacent femoral bone tissue, each of said distal sleeve members having a closed end portion that extends beyond the lower end of the distal stem portion;
    c) holding means for attaching a selected one of the sleeve members to the prosthesis body, the holding means including complimentary frustroconical surfaces on the upper end of each extension member and an annular surface on the prosthesis body;
    d) wherein the annular surface is closely positioned adjacent the thickened mid section; and
    e) the cylindrically-shaped distal stem portion and the distal sleeves being so configured that the hip prosthesis can be selectively used without a said distal sleeve if there is a proper fit without said sleeve.

2. The modular hip prosthesis of claim 1 wherein the distal stem extension member has a bore of a generally uniform cross-section along a majority of its length.

3. The modular hip prosthesis of claim 1 wherein the distal stem extension member is substantially straight.

4. The modular hip prosthesis of claim 1 wherein the distal stem extension member is curved to conform to the shape of the intramedullary canal.

5. The modular hip prosthesis of claim 1 wherein there are a plurality of proximal extension members of differing lengths.

6. The modular hip prosthesis of claim 1 wherein there are a plurality of distal extension members of differing lengths.

7. The modular hip prosthesis of claim 5 wherein at least one of the proximal extension members is a frustroconical tubular member having a smaller diameter end portion with a transversely extending annular portion at the end portion.

8. The modular hip prosthesis of claim 1 wherein the distal extension member has an upper end with a frustro-conically-shaped annular surface communicating with the bore.

9. The modular hip prosthesis of claim 5 wherein the prosthesis neck terminates at an upper end with a transverse flat surface at least some of the proximal extension members are of a length that places a portion of the proximal extension member beyond the upper end of the neck during use.

10. A modular hip prosthesis that can be custom fitted to a particular patient by a surgeon prior to surgical insertion, comprising:
    a) a hip prosthesis body having a proximal end portion with a neck portion for carrying a rounded head portion that fits the patient's acetabulum, a thickened mid-portion, and a cylindrically-shaped elongated distal stem portion having a lower end, said body being adapted for placement in the intramedullary canal of the patient's femur;
    b) a tubular stem extension sleeve having a hollowed portion generally complimentary in shape to the cylindrical distal stem and including a bore receptive of the stem said sleeve substantially covering said distal stem portion and including a closed lower end portion that extends below the lower end of the distal stem portion;
    c) attachment means for securing the extension sleeve and prosthesis body together at a position adjacent the mid-portion; and
    d) the attachment means comprising a frustroconically-shaped portion of the distal end portion that forms a friction fit with the top of the sleeve when the sleeve is loaded axially to the stem and the stem substantially occupies the bore.

11. The modular hip prosthesis of claim 10 wherein the distal stem extension has a bore of a generally uniform cross-section along a majority of its length.

12. The modular hip prosthesis of claim 10 wherein the distal stem extension member is substantially straight.

13. The modular hip prosthesis of claim 10 wherein the distal stem extension member is curved to conform to the shape of the intramedullary canal.

14. The modular hip prosthesis of claim 10 wherein the extension member has a longitudinally extending portion that increases flexibility of one portion of the extension member.

15. The modular hip prosthesis of claim 10 further comprising means for increasing the flexibility of one portion of the extension member along its length.

16. The modular hip prosthesis of claim 10 wherein the extension member has externally projecting means for engaging surrounding bone tissue.

17. The modular hip prosthesis of claim 15 wherein the flexibility increasing means comprises a longitudinally extending slot that extends along a portion of the extension member.

18. The modular hip prosthesis of claim 15 wherein the flexibility increasing means comprises a pair of intersecting slots, each extending longitudinally along a portion of the length of the extension member.

19. The modular hip prosthesis of claim 16 wherein the externally projecting means comprises a plurality of longitudinally extending and circumferentially spaced projections.

20. The modular hip prosthesis of claim 16 wherein the externally projecting means comprises a plurality of closely spaced longitudinally extending ridges of generally uniform size.

21. A modular hip prosthesis that can be custom fitted to a particular patient by a surgeon prior to surgical insertion, comprising:

a) a hip prosthesis body having an upper end portion with a neck adapted for carrying a removable rounded head portion that fits the patient's acetabulum, a mid-section with anterior and posterior sides and a lower stem portion adapted for placement in the intramedullary canal of the patient's femur;

b) removable proximal extension members of differing lengths, each selectively attachable to the neck for selectively conforming the prosthesis to the patient's adjacent acetabulum bone tissue by selectively increasing the length of the prosthesis neck to selectively space a rounded prosthesis head portion away from the mid portion along a line that intersects the patient's acetabular socket;

c) each extension member having holding means for attachment to the prosthesis body, the holding means including corresponding frustroconical surfaces on extension member and on the prosthesis body;

d) a rounded head prosthetic portion having a frustroconically shaped socket; and e) the extension members each having a frustroconical exterior surface that can form a tight fit with the external surface of a selected extension member.

22. The modular hip prosthesis of claim 21 wherein the extension member has a transverse portion at one end portion.

23. The modular hip prosthesis of claim 21 wherein the extension member has inner and outer frustroconical surfaces.

24. The modular hip prosthesis of claim 21 wherein at least some of the extension members have a transversely extending annular projecting portion at one end.

25. The modular hip prosthesis of claim 21 wherein there are a plurality of proximal extension members of differing lengths, some having transversely extending annular portions and some having open end portions.

26. The modular hip prosthesis of claim 21 wherein each of the plurality of extension members is sized to fit the neck of a single prosthesis body.

27. The modular hip prosthesis of claim 22 wherein at least one of the proximal extension members is a frustroconical tubular member having a smaller diameter end portion with a transversely extending annular portion at the end portion.

28. The modular hip prosthesis of claim 21 wherein the extension member and neck are each metallic in construction.

29. The modular hip prosthesis of claim 25 wherein the prosthesis neck terminates at an upper end with a transverse flat surface, and at least some of the proximal extension members are of a length that places a portion of the proximal extension member beyond the flat surface during use.

30. A modular hip prosthesis that can be custom fitted to a particular patient by a surgeon prior to surgical insertion, comprising:

a) a hip prosthesis body having a proximal end portion with a neck portion for carrying a rounded head portion that fits the patient's acetabulum, a thickened mid-portion, and a cylindrical distal stem portion having a lower end, said body being adapted for placement in the intramedullary canal of the patient's femur;

b) an elongated tubular stem extension sleeve extending substantially the full length of the distal stem portion, said sleeve having a hollowed portion generally complimentary in shape to the cylindrical distal stem and including a bore receptive of the stem, the stem extension having one end portion that is open, defining a socket that communicates with the bore and a second end portion that is closed for extending below the lower end of the distal stem portion;

c) attachment means positioned immediately adjacent the lower end of the mid-portion and the top of the distal stem portion for securing the extension sleeve and prosthesis body together; and d) the attachment means comprising a frustroconically-shaped portion on the upper end of the distal stem portion that forms a friction taper-lock fit with the top of the sleeve when the sleeve is loaded axially to the stem and the stem occupies at least a majority of the bore.

31. The modular hip prosthesis of claim 30 wherein the stem extension sleeve has a bore of a generally uniform cross-section along a majority of its length.

32. The modular hip prosthesis of claim 30 wherein the stem extension sleeve is substantially straight.

33. The modular hip prosthesis of claim 30 wherein the stem extension sleeve is curved to conform to the shape of the patient's intramedullary canal.

34. The modular hip prosthesis of claim 30 further comprising a slot that extends longitudinally along the length of the extension sleeve.

35. The modular hip prosthesis of claim 30 wherein the extension sleeve member further comprises externally projecting, longitudinally extending means for engaging surrounding bone tissue to prevent rotation of the stem and sleeve relative to the patient's bone tissue.

36. The modular hip prosthesis of claim 34 wherein there are a pair of intersecting, longitudinally extending slots that extends along a major portion of the length of each extension member.

37. The modular hip prosthesis of claim 34 wherein there are a pair of intersecting slots extending longitudinally along a portion of the length of the extension sleeve member.

38. The modular hip prosthesis of claim 35 wherein the externally projecting means comprises a plurality of longitudinally extending and circumferentially spaced projections on the outer surface of the extension sleeve member.

39. The modular hip prosthesis of claim 35 wherein the externally projecting means comprises a plurality of closely spaced longitudinally extending ridges of generally uniform size.

40. A modular hip prosthesis that can be custom fitted to a particular patient by a surgeon prior to surgical insertion, comprising:

a) a hip prosthesis body having a proximal end portion with a neck portion for carrying a rounded head portion that fits the patient's acetabulum, a transversely thickened mid-portion, and a cylindrical distal stem portion, said body being adapted for placement in the intramedullary canal of the patient's femur, the stem including a lower distal end portion that is hemispherically shaped;

b) a tubular stem extension sleeve extending substantially the full length of the distal stem portion, said sleeve having a hollowed portion generally complimentary in shape to the stem and including a bore receptive of the stem, the stem extension having one end portion that is open so that the stem can enter the bore at the opening and a second end portion that is closed, said second end portion comprising a hemispherically shaped lower distal end portion that extends below the lower end of the distal stem portion;

c) attachment means on the top of the distal stem positioned closely for securing the extension sleeve and prosthesis body together; and d) the attachment means including a beveled annular portion of the distal stem that forms a friction fit when the sleeve is loaded axially to the stem and the stem occupies the bore, and e) wherein the prosthesis body gradually increases in diameter proximally of the beveled annular portion to define the transversely thickened portion.

* * * * *